(12) United States Patent
Krzyzosiak et al.

(10) Patent No.: US 9,970,004 B2
(45) Date of Patent: May 15, 2018

(54) NUCLEIC ACID MOLECULE, EXPRESSION CASSETTE, EXPRESSION VECTOR, EUKARYOTIC HOST CELL, INDUCTION METHOD OF RNA INTERFERENCDE IN EUKARYOTIC HOST AND USE OF THE NUCLEIC ACID MOLECULE IN THERAPY OF DISEASES INDUCED BY EXPANSION OF TRINUCLEOTIDE CAG REPEATS

(71) Applicant: INSTYTUT CHEMII BIOORGANICZNEJ PAN, Poznan (PL)

(72) Inventors: Wlodzimierz Krzyzosiak, Poznan (PL); Marta Olejniczak, Poznan (PL); Paulina Galka-Marciniak, Zdunska Wola (PL); Agnieszka Fiszer, Dabrowka (PL)

(73) Assignee: INSTYTUT CHEMII BIOORGANICZNEJ PAN, Poznan (PL)

(*) Notice: Subject to any disclaimer, the term of this patent is extended or adjusted under 35 U.S.C. 154(b) by 0 days. days.

(21) Appl. No.: 14/916,039

(22) PCT Filed: Sep. 2, 2014

(86) PCT No.: PCT/PL2014/000100
§ 371 (c)(1),
(2) Date: Mar. 2, 2016

(87) PCT Pub. No.: WO2015/030616
PCT Pub. Date: Mar. 5, 2015

(65) Prior Publication Data
US 2016/0376586 A1    Dec. 29, 2016

(30) Foreign Application Priority Data
Sep. 2, 2013   (PL) .......................... 405224

(51) Int. Cl.
C07H 21/04        (2006.01)
C12N 15/113       (2010.01)

(52) U.S. Cl.
CPC ...... *C12N 15/113* (2013.01); *C12N 2310/141* (2013.01); *C12N 2310/334* (2013.01); *C12N 2310/335* (2013.01); *C12N 2310/336* (2013.01); *C12N 2310/531* (2013.01); *C12N 2310/533* (2013.01); *C12N 2320/34* (2013.01); *C12N 2330/51* (2013.01)

(58) Field of Classification Search
None
See application file for complete search history.

(56) References Cited

U.S. PATENT DOCUMENTS

| 8,481,710 B2 * | 7/2013 | Davidson | ............ C12N 15/113 |
| | | | 536/24.1 |
| 2006/0088837 A1 * | 4/2006 | Taira | .................. A01K 67/0275 |
| | | | 435/6.13 |

FOREIGN PATENT DOCUMENTS

| WO | 03/013437 A2 | 2/2003 |
| WO | 2006/031267 A2 | 3/2006 |
| WO | 2011/097388 A1 | 8/2011 |
| WO | 2012/109667 A1 | 8/2012 |
| WO | 2013/033223 A1 | 3/2013 |

OTHER PUBLICATIONS

Hu J et al: "Allele-Selective Inhibition of Huntingtin Expression by Switching to an miRNA-like RNAi Mechanism", Chemistry and Biology, vol. 17, No. 11, Nov. 24, 2010 (Nov. 24, 2010), pp. 1183-1188.
Agnieszka Fiszer et al: "An evaluation of oligonucleotide-based therapeutic strategies for poly0 diseases", Bmcmolecular Biology, vol. 13, No. 1, Mar. 7, 2012 (Mar. 7, 2012), p. 6.
Dongboyu et al: "Single-Stranded RNAs UseRNAi to Potently and Allele-Selectively Inhibit Mutant Huntingtin Expression", Cell, vol. 150, No. 5, Aug. 1, 2012 (Aug. 1, 2012), pp. 895-908.
A. Fiszer et al: "Self-duplexing CUG repeats selectively inhibit mutant huntingtin expression", Nucleic Acids Research, vol. 41, No. 22, Dec. 1, 2013 (Dec. 1, 2013), pp. 10426-10437.

\* cited by examiner

*Primary Examiner* — Kimberly Chong
(74) *Attorney, Agent, or Firm* — Arrigo, Lee, Guttman & Mouta-Bellum LLP

(57) ABSTRACT

Subjects of the invention are: nucleic acid molecule, expression cassette, expression vector, eukaryotic host cell, induction method of RNA interference in eukaryotic host and use of nucleic acid molecule in therapy of diseases induced by expansion of trinucleotide CAG-type repeats. Solution relates to the new concept of treating hereditary human neurological diseases caused by expansion of CAG-type trinucleotide repeats using RNA interference technology.

14 Claims, 4 Drawing Sheets

Figure 1:
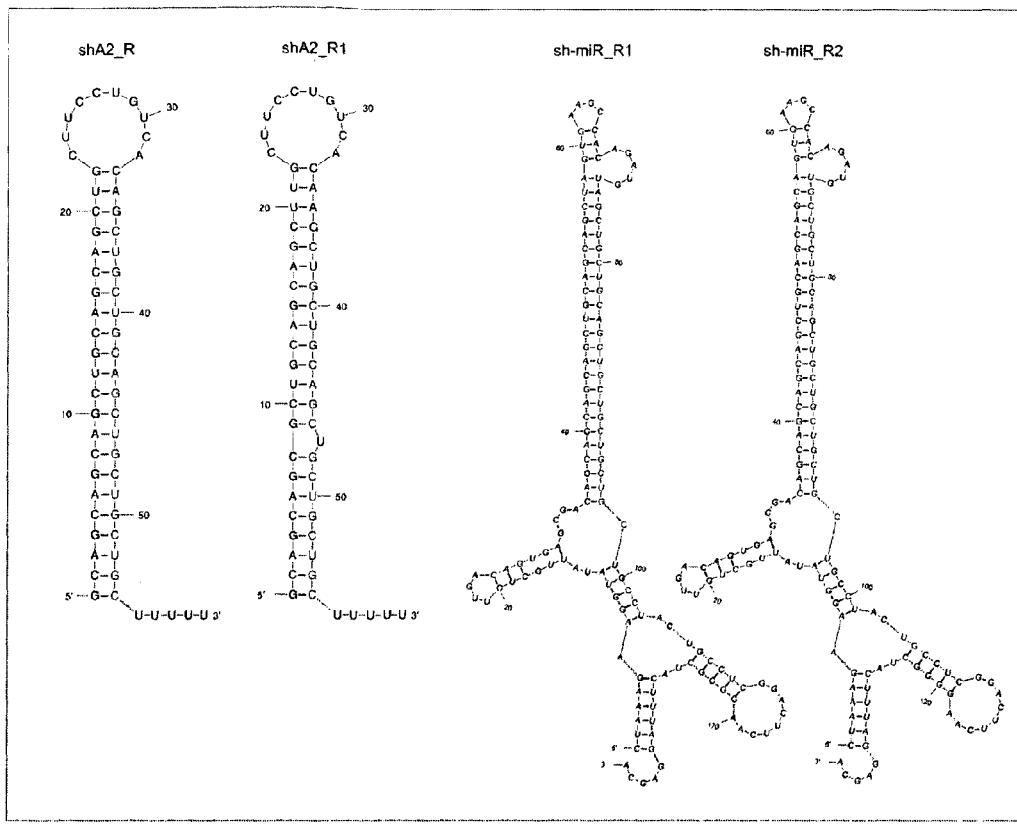

SEQUENCE LISTING

<160> NUMBER OF SEQ ID NOS: 23

<210> SEQ ID NO 1
<211> LENGTH: 22
<212> TYPE: RNA
<213> ORGANISM: artificial sequence
<220> FEATURE:
<223> OTHER INFORMATION: modified oligonucleotide

<400> SEQUENCE: 1
cugcugcagc ugcugcugcu gc         22

<210> SEQ ID NO 2
<211> LENGTH: 21
<212> TYPE: RNA
<213> ORGANISM: artificial sequence
<220> FEATURE:
<223> OTHER INFORMATION: modified oligonucleotide

<400> SEQUENCE: 2
gcugcugcag cugcugcugc u          21

```
<210> SEQ ID NO 3
<211> LENGTH: 22
<212> TYPE: RNA
<213> ORGANISM: artificial sequence
<220> FEATURE:
<223> OTHER INFORMATION: modified oligonucleotide

<400> SEQUENCE: 3
cugcugcagc ugcugcagcu gc                                             22

<210> SEQ ID NO 4
<211> LENGTH: 21
<212> TYPE: RNA
<213> ORGANISM: artificial sequence
<220> FEATURE:
<223> OTHER INFORMATION: modified oligonucleotide

<400> SEQUENCE: 4
gcugcugcag cugcagcugc u                                              21

<210> SEQ ID NO 5
<211> LENGTH: 21
<212> TYPE: RNA
<213> ORGANISM: artificial sequence
<220> FEATURE:
<223> OTHER INFORMATION: modified oligonucleotide

<400> SEQUENCE: 5
gcugcugcug cagcagcugc u                                              21

<210> SEQ ID NO 6
<211> LENGTH: 20
<212> TYPE: RNA
<213> ORGANISM: artificial sequence
<220> FEATURE:
<223> OTHER INFORMATION: modified oligonucleotide

<400> SEQUENCE: 6
ugcugcugcu gcagcagcug                                                20

<210> SEQ ID NO 7
<211> LENGTH: 21
<212> TYPE: RNA
<213> ORGANISM: artificial sequence
<220> FEATURE:
<223> OTHER INFORMATION: modified oligonucleotide

<400> SEQUENCE: 7
gcugcugcua agcagcugc u                                               21

<210> SEQ ID NO 8
<211> LENGTH: 22
<212> TYPE: RNA
<213> ORGANISM: artificial sequence
<220> FEATURE:
<223> OTHER INFORMATION: modified oligonucleotide

<400> SEQUENCE: 8
cugcugcggc ugcugcugcu gc                                             22

<210> SEQ ID NO 9
<211> LENGTH: 21
<212> TYPE: RNA
<213> ORGANISM: artificial sequence
<220> FEATURE:
```

<223> OTHER INFORMATION: modified oligonucleotide

<400> SEQUENCE: 9
gcugcugcgg cugcugcugc u                                              21

<210> SEQ ID NO 10
<211> LENGTH: 22
<212> TYPE: RNA
<213> ORGANISM: artificial sequence
<220> FEATURE:
<223> OTHER INFORMATION: modified oligonucleotide

<400> SEQUENCE: 10
cugcugcagc ugcugcggcu gc                                             22

<210> SEQ ID NO 11
<211> LENGTH: 21
<212> TYPE: RNA
<213> ORGANISM: artificial sequence
<220> FEATURE:
<223> OTHER INFORMATION: modified oligonucleotide

<400> SEQUENCE: 11
gcugcugcgg cugcggcugc u                                              21

<210> SEQ ID NO 12
<211> LENGTH: 21
<212> TYPE: RNA
<213> ORGANISM: artificial sequence
<220> FEATURE:
<223> OTHER INFORMATION: modified oligonucleotide

<400> SEQUENCE: 12
gcugcugcug cggcggcugc u                                              21

<210> SEQ ID NO 13
<211> LENGTH: 20
<212> TYPE: RNA
<213> ORGANISM: artificial sequence
<220> FEATURE:
<223> OTHER INFORMATION: modified oligonucleotide

<400> SEQUENCE: 13
ugcugcugcu gcggcggcug                                                20

<210> SEQ ID NO 14
<211> LENGTH: 22
<212> TYPE: RNA
<213> ORGANISM: artificial sequence
<220> FEATURE:
<223> OTHER INFORMATION: modified oligonucleotide

<400> SEQUENCE: 14
cugcugcggc ggcugcggcu gc                                             22

<210> SEQ ID NO 15
<211> LENGTH: 21
<212> TYPE: RNA
<213> ORGANISM: artificial sequence
<220> FEATURE:
<223> OTHER INFORMATION: modified oligonucleotide

<400> SEQUENCE: 15
gcugcugcgg cugcggcggc u                                              21

-continued

```
<210> SEQ ID NO 16
<211> LENGTH: 20
<212> TYPE: RNA
<213> ORGANISM: artificial sequence
<220> FEATURE:
<223> OTHER INFORMATION: modified oligonucleotide

<400> SEQUENCE: 16
ugcugcugcg gcggcggcug                                                     20

<210> SEQ ID NO 17
<211> LENGTH: 21
<212> TYPE: RNA
<213> ORGANISM: artificial sequence
<220> FEATURE:
<223> OTHER INFORMATION: modified oligonucleotide

<400> SEQUENCE: 17
gcugcugcug cggcggcggc u                                                   21

<210> SEQ ID NO 18
<211> LENGTH: 20
<212> TYPE: RNA
<213> ORGANISM: artificial sequence
<220> FEATURE:
<223> OTHER INFORMATION: modified oligonucleotide

<400> SEQUENCE: 18
ugcugcugcu gcggcggcgg                                                     20

<210> SEQ ID NO 19
<211> LENGTH: 22
<212> TYPE: RNA
<213> ORGANISM: artificial sequence
<220> FEATURE:
<223> OTHER INFORMATION: modified oligonucleotide

<400> SEQUENCE: 19
cugcugcugc ugcggcggcg gc                                                  22

<210> SEQ ID NO 20
<211> LENGTH: 20
<212> TYPE: RNA
<213> ORGANISM: artificial sequence
<220> FEATURE:
<223> OTHER INFORMATION: modified oligonucleotide

<400> SEQUENCE: 20
ugcugcugcg gcggcggcgg                                                     20

<210> SEQ ID NO 21
<211> LENGTH: 22
<212> TYPE: RNA
<213> ORGANISM: artificial sequence
<220> FEATURE:
<223> OTHER INFORMATION: modified oligonucleotide

<400> SEQUENCE: 21
cugcugcugc ggcggcggcg gc                                                  22

<210> SEQ ID NO 22
<211> LENGTH: 21
<212> TYPE: RNA
<213> ORGANISM: artificial sequence
<220> FEATURE:
<223> OTHER INFORMATION: modified oligonucleotide
```

```
<400> SEQUENCE: 22
gcugcugcug gggcggcugc u                                               21

<210> SEQ ID NO 23
<211> LENGTH: 10
<212> TYPE: RNA
<213> ORGANISM: artificial sequence
<220> FEATURE:
<223> OTHER INFORMATION: modified oligonucleotide

<400> SEQUENCE: 23
cuuccuguca                                                            10
```

NUCLEIC ACID MOLECULE, EXPRESSION CASSETTE, EXPRESSION VECTOR, EUKARYOTIC HOST CELL, INDUCTION METHOD OF RNA INTERFERENCDE IN EUKARYOTIC HOST AND USE OF THE NUCLEIC ACID MOLECULE IN THERAPY OF DISEASES INDUCED BY EXPANSION OF TRINUCLEOTIDE CAG REPEATS

Subjects of the invention are: Nucleic acid molecule, expression cassette, expression vector, eukaryotic host cell, induction method of RNA interference in eukaryotic host and use of nucleic acid molecule in therapy of diseases induced by expansion of trinucleotide CAG repeats. Solution relates to new concept of treating hereditary human neurological diseases caused by expansion of CAG trinucleotide repeats, with the use of RNA interference technology.

The predominant part of human genome consists of different types of repetitive sequences. These elements are present in both coding and non-coding sequences of genes, as well as in intergenic regions. Expansion of unstable trinucleotide repetitive sequences in single genes is the cause of over 20 different hereditary diseases, known as Triplet Repeat Expansion Diseases (TREDs). These are neurodegenerative diseases, which are incurable so far.

Most of TREDs-associated genes contain CAG-triplet repeat tracts in coding region, and number of repeats causing disease ranges between 40 and 100. Examples of such diseases are Huntington Disease (HD) and a number of spinocerebellar ataxias e.g. spinocerebellar ataxia type 3 (SCA3). Protein containing toxic polyglutamine tract, which changes proper protein function, is produced as a translation result of mutant transcript. Expanded CAG repeat tracts can also activate pathogenic mechanisms at RNA level, including sequestration of specific proteins by mutant transcripts.

Most diseases caused by expansion of trinucleotide repeats is autosomal-dominantly determined. Every cell contains both normal and mutated gene variant. Products of mutant gene, transcript and protein, are toxic for cell, therefore their removal should prevent of the disease. The normal protein is essential for proper cell functioning, therefore therapeutical strategies should be based on allele-selective elimination of mutant variant. This effect can be achieved by targeting regions which distinguish between both gene alleles, single-nucleotide polymorphisms (SNPs) or short tandem repeats (STR), using therapeutic reagents. Methods of mutant transcript and protein elimination published so far are using mainly antisense oligonucleotides and RNA interference technology reagents of siRNA type (short interfering RNA).

RNA interference (RNAi) is a natural cellular process taking part in regulation of gene expression and it is also a mechanism of defense against viruses and mobile genomic elements. The basis for RNA interference is the participation of short double-stranded RNA molecules (dsRNA), 20-30 nucleotide long, in selective silencing of gene expression. Those molecules have sequences that are complementary to sequences within mRNA, which, as a result of interactions between them, leads to degradation of transcript or to translation inhibition, depending on the level of complementarity. DsRNA taking part in RNAi pathway are produced in cell as a result of the processing of longer hairpin structured precursor molecules by endogenous enzymatic machinery. RNAi technology uses synthetic siRNA-type reagents (short interfering RNA), vector shRNA-type reagents (short hairpin RNA, reagents mimicking microRNA precursors) or sh-miR (reagents mimicking primary microRNA transcripts). Active strand of siRNA duplex is known as a guide strand, whereas complementary strand is known as a passenger strand. Application of suitable vectors and promoters gives the possibility to regulate expression of interfering RNA of shRNA- and sh-miR-type, selective delivery of them into the tissues of interest and most of all long-term silencing effect.

In Yu D. et al. [1] and Lima W F. et al. [2] allele-selective silencing of mutant HTT gene responsible for Huntington disease has been demonstrated using chemically modificated oligonucleotides directed against a mutant CAG tract. In Hu et al. [3,4] short, synthetic RNA duplexes have been used for selective inhibition of mutant huntingtin with the participation of RNA interference mechanism.

In WO 2010/014592 patent application (published 2010 Feb. 4), method of selective inhibition of expression for the protein containing expanded polyglutamine tract using chemically modified oligonucleotides has been described. Described nucleic acid analogues are 7-30 bases long and are directed against expanded CAG-repetition fragment of mutant transcript. Application in particular relates to PNA and LNA oligomers and their possible application in inhibition of translation of the following proteins associated with polyglutamine diseases: huntingtin, ataxin-3, ataxin-1, ataxin-2, atrophin-1.

WO 2011/097641 patent application (published 2011 Aug. 11) comprises chemically modified oligonucleotides, 13-22 bases long and with sequence fully complementary to CAG-repeat region. Molecules included in the patent application can contain modified internucleoside bond or sugar residue. It comprises the possibility of application of a number of substituents in any positions, and it especially comprises LNA, Cet, ENA, MOE modifications. Their usage is claimed for all polyglutamine diseases.

In WO 2011/097388 patent application (published on 2011 Aug. 11), usage of double-stranded RNA for selective expression inhibition of proteins containing polyglutamine tract has been described. Molecules described in application are double-stranded RNA, 15-30 bases long, directed against expanded CAG repeat tracts. Oligonucleotides sequence is characterised in that it contains no more than one substitution in seed sequence and 1 to 5 freely located substitutions in remaining region of molecule. Double-stranded RNA described in application can contain one or more chemically modified base. Application relates to possible usage of those molecules in inhibition of translation of the following proteins associated with polyglutamine diseases: huntingtin, ataxin-3, ataxin-1, ataxin-2 and atrophin-1. Application comprises usage of the described molecules in inhibition of polyglutamine proteins in cells and different methods of their application in vivo.

WO 2013/033223 patent application (published on 2013 Mar. 7) relates to the method of use of single-stranded oligonucleotides with sequence complementary to expanded trinucleotide repeats region (CAG, CUG, CGG, GCC and GAA). Oligonucleotides described in patent application may be 13-30 bases long and can contain number of chemical modifications (stabilising 5'-end phosphate group of nucleotide, substituents in internucleoside bond and sugar residue). Additionally, oligonucleotide can contain 1 to 5 substitutions in sequence, which leads to formation of non-canonical base pairs in interactions with the repeat tract sequence of interest. It is recommended to show at least 5-fold selectivity in silencing of mutant allele expression in comparison with normal allele. Usage of described oligonucleotides is claimed both for cell cultures, animal models as well as for patients.

In US2005255086 (published 2005 Nov. 17) and WO2006031267 patent applications (published 2006 Mar. 23) method using RNAi in vivo for dominant neurodegenerative diseases therapy has been described. This solution relates to short interfering RNAs directed against Hunginton disease gene, spinocerebellar ataxia type 1 (SCA1), methods of usage and vector systems for those molecules.

In WO2004047872 (published 2004 Jun. 10), EP2145628 (published 2012 Mar. 21) patent applications, neurodegenerative diseases treatment method through intracerebral siRNA delivery has been described. In this application method, short interfering RNA and method of neurodegenerative disease treatment comprising steps of surgical catheter implantation, in such a way that releasing part was placed adjacent to specific infusion region in brain, and was releasing through emitting part of catheter specified dose of at least one substance capable to inhibit production of at least one neurodegenerative protein, have been described. The present invention describes also vectors encoding short interfering RNA and treatment methods of neurodegenerative diseases such as Alzheimer, Parkinson, Huntington disease, spinocerebellar ataxia type 1, 2 and 3 and/or DRPLA (dentatorubral-pallidoluysian atrophy).

In US2006270623 (published 2006 Nov. 30) and US2005277133 patent application (published 2005 Dec. 15), method of treatment of diseases associated with polyglutamine repeats expansion based on RNAi phenomenon using short interfering nucleic acid (siNA) has been described. This solution relates to compounds, their composition, research methods, diagnosis, treatment of diseases and conditions related to different polyglutamic repeats allelic variants responsible for modulation of gene expression and/or their activity. This disclosure especially relates to short nucleic acids molecules, such as short interfering nucleic acids (siNA), short interfering RNA (siRNA), double-stranded RNA (dsRNA), micro-RNA (miRNA) and short hairpin RNA (shRNA), molecules capable of mediation in RNA interference process directed against expression of genes correlated with diseases or alleles encoding poliQ sequences.

In WO2012109667 patent application (published 2012-18-16), method of delivery of therapeutic RNAi reagents into the cells affected by pathogenesis in Huntington disease has been described. Construction method of expression cassettes used for releasing therapeutical siRNA molecules with the possibility of introducing them into cells in virus vectors has been described in detail. In the described approach to the construction of expression cassettes, sequences of natural miRNA precursors have been used providing reduction of released siRNA molecules' toxicity through reduction of ability to cause off-target effects.

In US2013065298 (published 2013 Mar. 14), US2004241854 (published 2004 Dec. 2), US2011244561 (published 2011 Oct. 6), U.S. Pat. No. 8,329,890 (published 2012 Dec. 11) patent applications, a method, based on RNAi phenomenon, of allele-selective silencing of mutant gene variants being cause of group of diseases inherited in dominant manner, including Huntington disease and a number of spinocerebellar ataxias, has been described. The described invention assumes usage of reagents in form of siRNA, shRNA or miRNA aiming at mRNA region distant from trinucleotide repeats tract, but containing single-nucleotide polymorphisms (SNPs) which enable differentiation between mutant and wild-type allele and further preferential silencing of its expression.

In US2011212520 (published 2011 Sep. 1) and US2008274989 (published 2008 Nov. 6) patent applications, method of RNAi reagents usage in neurodegenerative disease therapy in vivo has been described. Those applications contain description of RNAi reagents application method to prevent accumulation of mutant proteins: huntingtin and ataxin-1. This disclosure relates also to introduction of therapeutical molecules, both in RNA form, as well in genetic vector forms (including viral—AAV), to different regions of central nervous system in which lesions are observed.

In US2008/0015158 A1 patent application (published 2008 Jan. 17) gene HTT expression inhibition method using dsRNA inhibitors targeting in sequence specific for HTT gene, located just before CAG repeat tract, has been described.

Despite solutions existing up to now describing methods of RNAi reagents usage in therapy of neurodegenerative diseases, there is still a need for a allele-selective silencing of genes containing mutant CAG tracts using vector reagents targeting directly into repeat region.

The aim of present invention is selective silencing of the expression of mutant genes responsible for polyglutamine diseases through targeting at CAG-repeats region in transcripts (universal character of the solution) using RNAi-based vector reagents (long-term therapeutic effect). The solution according to the invention comprises shRNA inhibitors (short RNA hairpins) and sh-miR (artificial miRNA) resembling the structure of miRNA precursor molecules (accordingly pre-miRNA and pri-miRNA), from which, as a result of cellular biogenesis, heterogenous pool of interfering RNA is released, which inhibits the expression of mutant genes, such as HTT and ATXN3.

Surprisingly, it turned out that the solution according to the invention relates to new concept of treating congenital human neurological disease caused by expansion of CAG-type trinucleotide repeats using RNA interference technology.

Cellular biogenesis of interference RNA of shRNA type and sh-miR includes i.a. transcription using RNA II or III polymerase and generation of hairpin structured molecules. These structures are cut in cells by endogenous proteins by Microprocessor complex (refers to sh-miR type reagents), which are transported from nucleus to cytoplasm and cut by Dicer nuclease (refers to shRNA, sh-miR reagents) to pool of short RNA duplexes, 21-23 base pairs long. In the next step, short RNA duplexes are bound by specific proteins and one strand of the duplex (guide strand) is used to recognise sequence in the transcript of interest.

The subject of the invention is nucleic acid molecule composed of duplex and loop, in which one of the duplex strand, guide strand, contains sequence specified by a sequence chosen from SEQ ID No. 1-22, and second strand from the duplex, passenger strand, is complementary in at least 80%, wherein nucleic acid molecule forms hairpin structure in the cell.

Preferable when duplex region is 19-30 base pairs long.
Preferable when first and second strand of the duplex is connected by a loop 4 to 15 nt long.
Preferable when loop is specified by a sequence SEQ ID No. 23.
Preferable when a molecule contains in the guide strand modified CUG-type repeats containing 1, 2, 3, or 4 substitutions causing formation of non-canonical base pairs by interaction with targeted CAG sequence in transcripts.
Preferable when molecule contains flanking sequences 5' and 3' derived from natural miRNA, wherein precursor flanking sequences of natural length are shortened or not.

Preferable when molecule contains loop sequence derived from natural miRNA.

Another subject of the invention is expression cassette containing regulated or constitutive promoter, characterised in that it is functionally associated with sequence coding nucleic acid specified above.

Preferable when a promoter is polII or polIII RNA promoter.

Another subject of the invention is expression vector characterised in that it contains expression cassette specified above.

Preferable when it is adenoviral, lentiviral, adeno-associated (AAV), polio- or HSV vector.

Another subject of the invention is eukaryotic host cell characterised in that it contains molecule of nucleic acid specified above.

Another subject of the invention is cell characterised in that it contains expression cassette specified above.

Another subject of the invention is eukaryotic host cell characterised in that it contains expression vector specified above.

Another subject of the invention is a method of RNA interference induction in eukaryotic host, characterised in that it comprises delivery of effective dose of the nucleic acid molecule specified above, expression cassette specified above, vector specified above to the examined subject.

Another subject of the invention is usage of nucleic acid molecule specified above, expression cassette specified above, vector specified above or cells specified above in a therapy of neurological diseases induced by the expansion of trinucleotide CAG repeats.

Another subject of the invention is usage of nucleic acid molecule specified by claims given above, expression cassette specified above, vector specified above or cells specified above in production of medicine for a therapy of neurological diseases induced by the expansion of trinucleotide CAG repeats.

Preferably when it is used in the therapy of human neurodegenerative diseases such as Huntington disease or spinocerebellar ataxia type 3 caused by CAG triplet expansions in single genes.

The attached Figures facilitate a better understanding and present the nature of the invention:

FIG. 1 shows examples of the sequence and structure of the shRNA- and sh-miR-type interfering RNAs.

Interfering RNAs are formed in cells as a result of transcription. They are forming hairpin-type structure with double-stranded stem and loop. Interfering RNA of shRNA-type contain few uridyl residues on the 3' end and sequence of the guide strand, which recognises the sequence of interest (red color), is located preferentially in the 3' arm of the hairpin stem. Sh-miR type interfering RNA contains additional loop and flanking 5' and 3' sequences of the natural microRNA.

Figure 2:
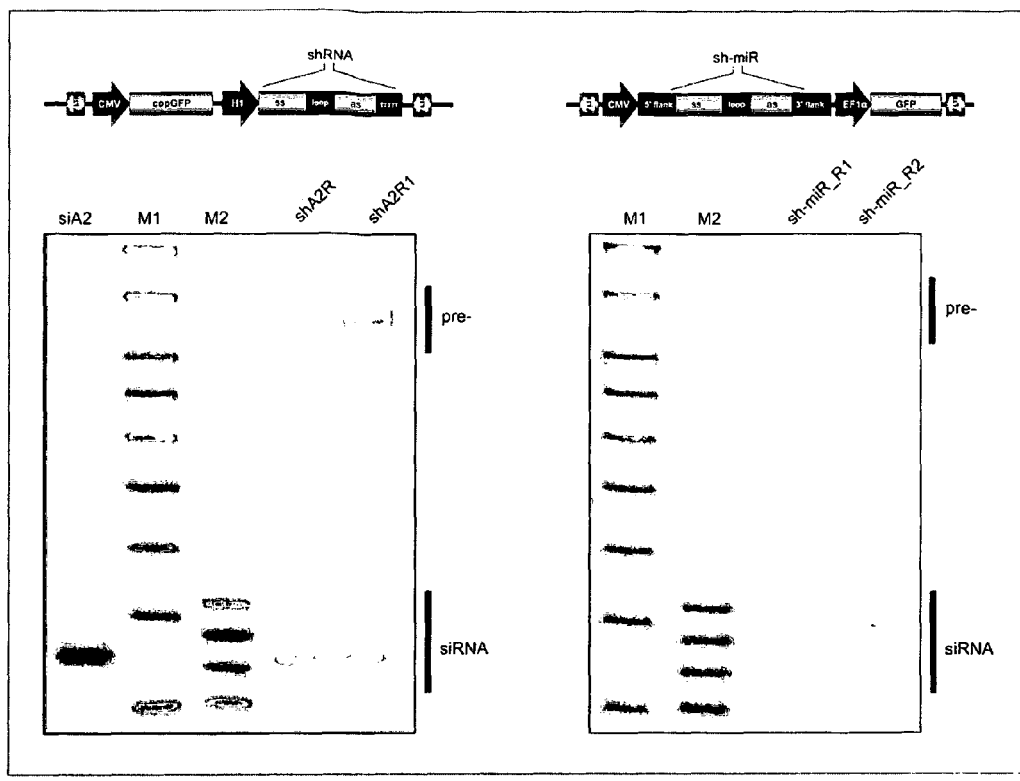

FIG. 2 shows interfering RNA processing in HEK 293 cells by Dicer RNase. Molecules of interfering RNA directed against mutant CAG tracts in transcripts are introduced to the cells in the form of expression cassettes containing, besides sequence coding shRNA or sh-miR, also reporter gene sequence, such as copGFP or GFP. Using method of high-resolution northern-type hybridisation, formation of transcripts in cells (pre-) or their cutting by Dicer RNase to the pool of short RNA duplexes (siRNA) has been proved. Both the transcript being formed as well as short siRNA duplexes are heterogenous. M1 and M2 stands for RNA length markers; siA2—synthetic siRNA transfected into cells.

Figure 3:
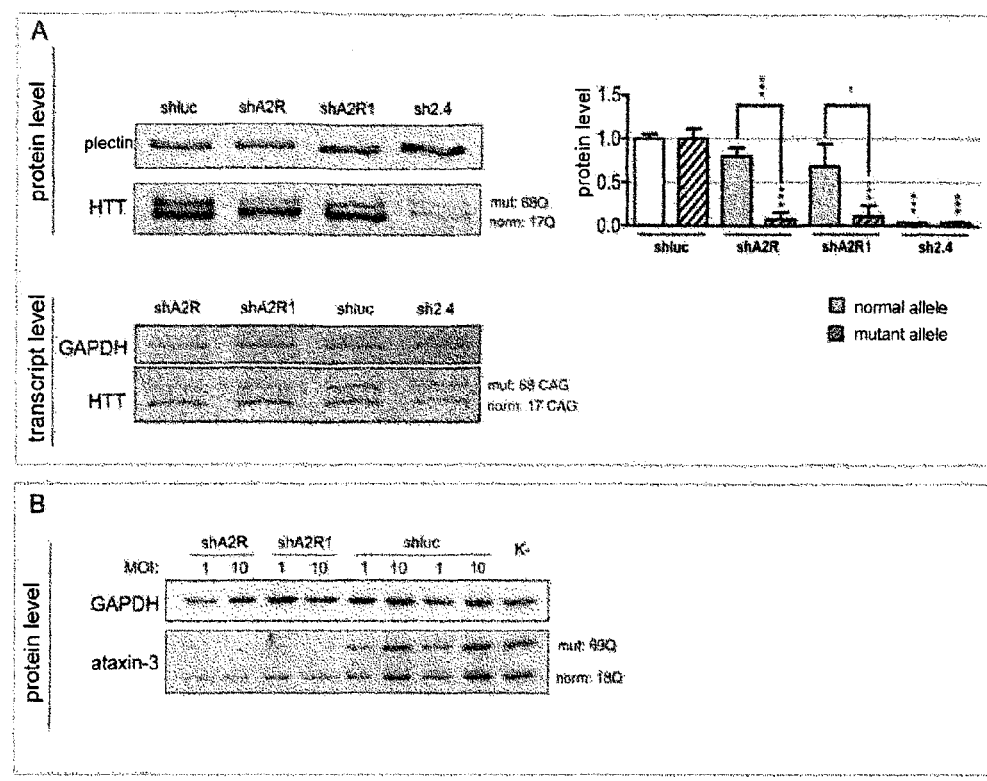

FIG. 3 shows allele-selective silencing of the huntingtin protein and ataxin 3 (assessed by Western blotting) and transcript of the HTT gene (assessed by RT-PCR) by shRNA-type interfering RNA.

A) Human fibroblasts derived from a patient with Huntington disease (containing 17/68 CAG repeats in HTT gene) were transduced using lentiviral vectors encoding shRNA-type interfering RNA. Cells were infected using MOI 10 amount of virus (multiplicity of infection) and analysed 7 days after infection. shLuc—negative control, shRNA directed against Luc gene, sh2.4—positive control, shRNA directed against specific sequence of the HTT gene; signals intensity from huntingtin protein were normalised to the level of plectin protein and shLuc control, statistic analyses were used for comparison (one-sample t-test). Error bars present standard deviations. Statistically significant values (p-value) are marked with asterisk.

Figure 4:
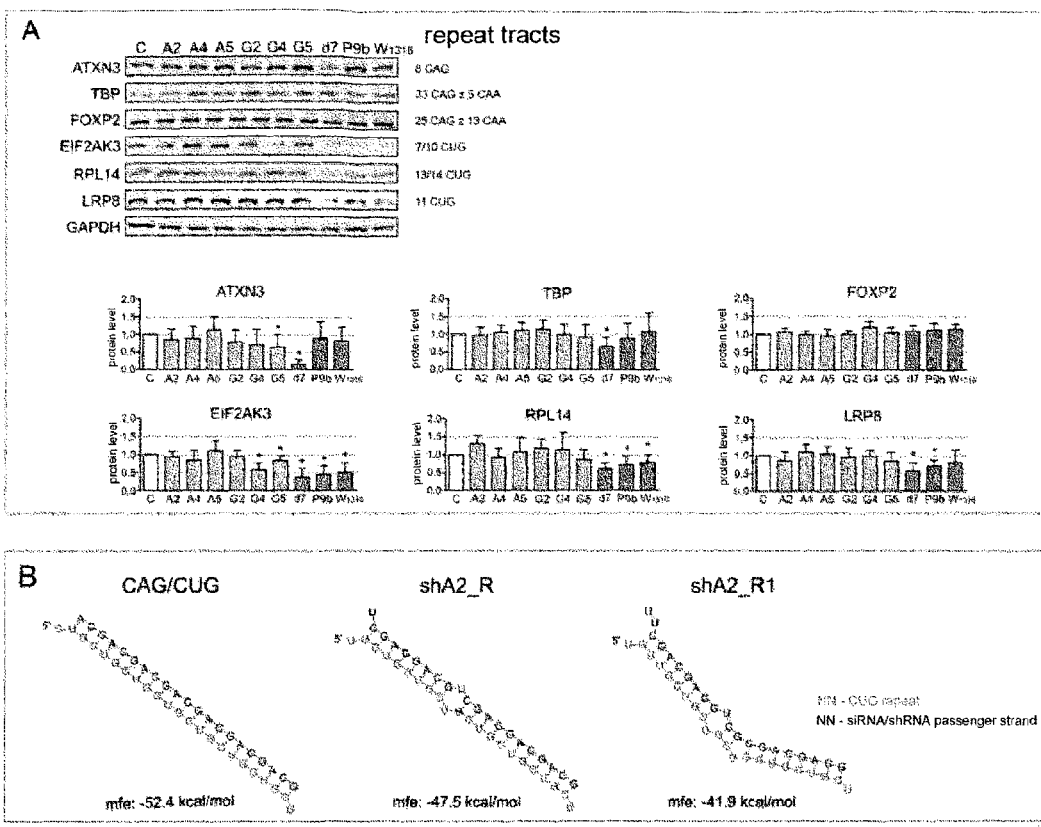

B) Human fibroblasts derived from a patient with spinocerebellar ataxia type 3 (containing 18/69 CAG in ATXN3 gene) were transduced using lentiviral vectors encoding shRNA-type interfering RNA (shA2R and shA2R1). Cells were infected using two virus concentrations (MOI 1 and 10) and analysed 7 days after infection. shLuc—negative control, shRNA directed against Luc gene, K—cells not transduced with virus. GAPDH—reference protein FIG. 4 shows analysis of interfering RNA silencing selectivity, for RNAs forming mismatches with CAG sequence of interest.

a) Western blotting analysis of ATXN3, TBP, FOXP2, EIF2AK3, RPL14 i LRP8 protein levels in HD fibroblasts 72 h after transfection using 50 nM RNA duplexes consisting of modified CUG repeats forming mismatches with CAG sequence of interest (reference reagents: d7, P9b and W 13/16). Nucleotide sequences of repeat tracts in genes encoding analysed proteins comprise: tracts for TBP (CAG)3(CAA)3(CAG)9(CAA)(CAG)(CAA)(CAG)20 and FOXP2: (CAG)4(CAA) (CAG)4(CAA)2(CAG)2(CAA)2(CAG)3 (CAA)5(CAG)2(CAA)2(CAG)5(CAA)(CAG)5. C—reference value defining expression level in cells transfected using control siRNA. Intensivities of signals were normalised to the level of reference protein GAPDH and compared using statistical test (one-sample t-test). Error bars show standard deviations. Statistically significant values are marked with asterisk (* p<0.05).

b) in comparison to unmodified molecules CAG/CUG, modifications of CAG repeats tract in passenger strand of interfering RNA reduced their possibility of binding and non-specific activity in RNAi pathway towards CUG transcripts; mfe—minimum free energy.

Below are example embodiments of the present invention described above.

EXAMPLES shRNA- and sh-miR-Type Interfering RNA Containing Modified CAG/CUG Sequences in the Structure of Hairpin Stem are Substrates for Dicer RNase In order to assess if interfering RNA are further processed in cells by proteins of RNAi pathway, HEK293 cells were transfected using expression vectors encoding shRNA and sh-miR molecules (FIG. 2). After 24 h, total RNA was isolated and separated in polyacrylamide gel and further hybridisation with probe in order to visualise transcripts and their cut products was performed (northern blot analysis). It was determined that interference RNAs produced in cells are cut by Dicer RNase to the pool of short heterogenous siRNA molecules. Furthermore, RNA-H1 shRNA molecules produced under control of polymerase III promoter are heterogeneous already at the transcript level (marked as a pre-), which is mainly due to presence of different length urydil residues at 3' end.

shRNA-Type Interference RNA Lead to Allele-Selective Silencing of Mutant Proteins Huntingtin and Ataxin-3.

In order to test the efficiency of shRNA-type interference RNA forming selective mismatches with CAG sequence of interest, lentiviral vectors encoding shA2R and shA2R1 molecules were constructed (containing ID. NO.1 and ID. NO.2 sequences from the Table). Human fibroblasts derived from patients with Huntington disease and spinocerebellar ataxia type 3 were transduced using lentiviruses in MOI 10 or 1 concentration and analysed 7 days after transduction (FIG. 3). Isolated protein was further analysed using Western Blotting and silencing level of mutant and normal variant was assessed in comparison with reference proteins and negative controls. Both analysed reagents lead to allele-selective silencing of mutant huntingtin, leaving non-mutant protein on normal level (FIG. 3A). HTT gene transcript analysis proved silencing selectivity of mutant form. Silencing efficiency of interfering RNAs was also tested on different model of polyglutamine diseases—SCA3 (FIG. 3B). Analysed molecules lead to allele-selective silencing of mutant ataxin-3 for both analysed virus concentrations (MOI 1 and MOI 10).

Methods

Cell Cultures and Transfection

Fibroblasts derived from the patients with HD (GM04281—17/68 CAG repeats in HTT gene) and SCA3 (GM06153—18/69 CAG repeats in ATXN3 gene) were obtained from Coriell Cell Repositories (Camden, N.J., USA). Cells were cultured in MEM medium (Lonza; Basel, Switzerland) enriched with 8% FBS (Sigma-Aldrich; St. Louis, USA), antibiotics: penicillin, streptomycin, amphotericin B (Sigma-Aldrich) and amino acids (Cat. no. M7145, Sigma-Aldrich). Transfection was performed using Lipofectamine 2000 (Life Technologies; Grand Island, N.Y., USA) according to the manufacturer recommendations.

Western Blotting

Western blot analysis for HTT protein (tract 17/68Q). Briefly, 25 µg of total protein was resolved in polyacrylamide gel with SDS (1.5 cm, 4% stacking gel/4.5 cm, 5% separation gel, acrylamide/bisacrylamide ratio—35:1) in XT Tricine buffer (Bio-Rad; Hercules, Calif., USA) under 140 V in water bath. Subsequently, proteins were transferred onto nitrocellulose membrane (Sigma-Aldrich). All immunodetection steps were performed using SNAPid system (Millipore; Billerica, Mass., USA) in PBS/0.9% NaCl/0.1% Tween-20 buffer and 0.25% skim milk. Immunofluorescence reaction was detected using ECL Western Blotting Substrate (ThermoScientific, Rockford, Ill., USA). Protein bands were scanned directly from membrane using camera and analysed using Gel-Pro Analyzer software. Western blot analysis for ATXN3 protein—25 µg of total protein was separated in polyacrylamide gel with SDS (5% stacking gel, 12% separation gel) in Laemmli buffer under 120V. Other steps of analysis as before.

Northern Blotting

Effector molecules released from vectors have been detected using northern-type hybridisation. Total RNA was isolated from HEK293T cells using TRI Reagent (BioShop; Burlington, Canada) according to the manufacturer recommendations. RNA (35 µg) was separated in denaturing polyacrylamide gel (12% PAA, 19:1 acrylamide/bis, 7.5 M urea) in 0.5×TBE buffer. RNA was transferred onto GeneScreen Plus (PerkinElmer) hybridisation membrane using semi-dry electrontransfer technique (Sigma-Aldrich). Membrane was hybridised with radioactively labelled DNA probe complementary to interfering RNA molecule. Radioactive signals were detected quantitatively using laser scanner FLA5100 (Multi Gauge v3.0, Fujifilm).

RT-PCR and RNA Isolation

Total RNA was isolated from cells using TRI Reagent (BioShop; Burlington, Canada) according to the manufacturer recommendations. RNA concentration was measured using NanoDrop spectrophotometer. 500 ng RNA was used for reverse transcription reaction, reaction was performed in 55° C. using Superscript III (Life Technologies) and random hexameres (Promegal Madison; Wis.; USA). PCR products were separated in 1.5% agarose gels in 0.5×TBE buffer and were dyed using ethidium bromide.

Plasmids and Virus Vectors

Expression cassettes encoding interfering RNA were containing H1 promoter, sequence of sense strand; loop sequence; antisense strand sequence and terminator sequence consisting of 5 uridines. Vector was also encoding reporter gene sequence copGFP from CMV promoter or GFP from EF1α promoter. Expression cassettes encoding interfering RNA were generated using DNA oligonucleotides (Sigma-Aldrich). Oligonucleotides DNA pairs were ligated into pGreenPuro expression plasmid (System Biosciences) and construct sequence was confirmed using sequencing.

Virus Assembly and Fibroblasts Transduction

In order to produce lentiviral vectors, plasmids containing expression cassettes with interfering RNA were cotransfected into HEK293TN cells with packaging plasmids pPACKH1-GAG, pPACKH1-REV and pVSV-G (System Biosciences). Medium with lentivirus was harvested on 2 and 3 day, filtered. Lentivirus particles were concentrated using PEGit Virus Precipitation Solution (System Biosciences). Lentiviral vectors were resuspended in Opti-MEM medium (Gibco) and amount of virus particles was tested (TU/ml) using flow cytometry (Accuri C6, BD Biosciences), basing on expression of reporter gene copGFP or GFP. Fibroblasts were transduced using MOI (multiplicity of infection) 1 and 10 in presence of polybrene (4 µg/ml).

SUMMARY

In previously described publications and patents there is no solution showing usage of RNAi technology vector reagents for selective silencing of mutant genes containing expanded CAG tracts targeting directly at mutation region. In contrast to previously proposed solutions, interfering RNA being subject of the application acts in highly allele-selective way preferentially silencing expression of mutant alleles aiming at CAG repeats. This effect was obtained thanks to the introduction of specific substitutions into the sequence of interfering RNA, which leads to formation of non-canonical base pairs in interaction with CAG sequence of interest. Interference RNAs pool produced during cellular biogenesis selectively lowers level of mutant proteins leaving wild-type proteins on normal level. Proposed solution reduces also off-target effect, which relies on non-specific activity of interference RNA towards other transcripts containing short CAG and CUG repeats. The use of viral vectors gives an opportunity to deliver interfering RNA to hardly-accessible tissues such as brain. Moreover, in contrast to approaches employing synthetic RNAi molecules, it gives a possibility for a long-term expression of interference RNA in affected tissue without need of multiple administration repeats.

Therapeutic approaches which employ aiming at the repeat sequences in poliQ diseases are more universal in comparison with aiming at the gene-specific sequences, and even more at polymorphic SNP sequences. Versatility of the invention is based on the targeting of interference RNA at mutant CAG-repeat sequences present in at least 9 polyglutamine diseases.

Sequence list

| SEQ. ID No. | 5'-3'Guide strand sequence | Number of mismatches with CAG sequence of interest | Type of mismatches with sequence of interest |
|---|---|---|---|
| 1 | CUGCUGCAGCUGCUGCUGCUGC | 1 | A:A |
| 2 | GCUGCUGCAGCUGCUGCUGCU | 1 | A:A |
| 3 | CUGCUGCAGCUGCUGCAGCUGC | 2 | A:A |
| 4 | GCUGCUGCAGCUGCAGCUGCU | 2 | A:A |
| 5 | GCUGCUGCUGCAGCAGCUGCU | 2 | A:A |
| 6 | UGCUGCUGCUGCAGCAGCUG | 2 | A:A |
| 7 | GCUGCUGCUAAAGCAGCUGCU | 4 | A:A |
| 8 | CUGCUGCGGCUGCUGCUGCUGC | 1 | A:G |
| 9 | GCUGCUGCGGCUGCUGCUGCU | 1 | A:G |
| 10 | CUGCUGCAGCUGCUGCGGCUGC | 2 | A:G |
| 11 | GCUGCUGCGGCUGCGGCUGCU | 2 | A:G |
| 12 | GCUGCUGCUGCGGCGGCUGCU | 2 | A:G |
| 13 | UGCUGCUGCUGCGGCGGCUG | 2 | A:G |
| 14 | CUGCUGCGGCGGCUGCGGCUGC | 3 | A:G |
| 15 | GCUGCUGCGGCUGCGGCGGCU | 3 | A:G |
| 16 | UGCUGCUGCGGCGGCGGCUG | 3 | A:G |
| 17 | GCUGCUGCUGCGGCGGCGGCU | 3 | A:G |
| 18 | UGCUGCUGCUGCGGCGGCGG | 3 | A:G |
| 19 | CUGCUGCUGCUGCGGCGGCGGC | 3 | A:G |
| 20 | UGCUGCUGCGGCGGCGGCGG | 4 | A:G |
| 21 | CUGCUGCUGCGGCGGCGGCGGC | 4 | A:G |
| 22 | GCUGCUGCUGGGGCGGCUGCU | 4 | A:G |

SEQ.ID No. 23
5' CUUCCUGUCA 3'

REFERENCES

1. Yu D, Pendergraff H, Liu J, et al. Single-Stranded RNAs Use RNAi to Potently and Allele-Selectively Inhibit Mutant Huntingtin Expression. Cell 2012; 150:895-908.
2. Lima W F, Prakash T P, Murray H M, et al. Single-stranded siRNAs activate RNAi in animals. Cell 2012; 150:883-894.
3. Hu J, Liu J, Corey D R. Allele-selective inhibition of huntingtin expression by switching to an miRNA-like RNAi mechanism. Chem Biol. 2010 Nov. 24; 17(11): 1183-8.
4. Hu J, Liu J, Yu D, Chu Y, Corey D R. Mechanism of allele-selective inhibition of huntingtin expression by duplex RNAs that target CAG repeats: function through the RNAi pathway. Nucleic Acids Res. 2012 December; 40(22):11270-80.

The invention claimed is:

1. A method of inhibiting expression of a mutant CAG expanded gene allele in a cell, comprising:
   introducing a nucleic acid molecule comprising a duplex and a loop into the cell;
   wherein the first strand of the duplex, the guide strand, comprises a sequence chosen from SEQ ID NO: 1 and SEQ ID NO: 2;
   wherein the second strand of the duplex, the passenger strand, is at least 80% complementary to the first strand; and
   wherein the nucleic acid molecule forms a hairpin structure in the cell.

2. The method of claim 1, wherein the nucleic acid molecule comprises a duplex region is from 19 to 30 base pairs long.

3. The method of claim 2, wherein the first and second strands of the duplex are connected by a loop that is from 4 to 15 nucleotides long.

4. The method of claim 2, wherein the loop has the sequence of SEQ ID NO: 23.

5. The method of claim 3, wherein the nucleic acid molecule comprises modified CUG-type repeats in the guide strand containing 1, 2, 3, or 4 substitutions and causing formation of non-canonical base pairs by interaction with targeted CAG sequences in transcripts.

6. The method of claim 1, wherein the nucleic acid molecule comprises 5' and 3' flanking sequences derived from a natural miRNA, wherein precursor flanking sequences of natural length are shortened or not.

7. The method of claim 6, wherein the nucleic acid molecule comprises a loop sequence derived from a natural miRNA.

8. The method of claim 1, wherein the nucleic acid molecule is introduced into the cell by expressing an expression cassette comprising a regulated or constitutive promoter, characterized in that it is functionally connected with a sequence encoding the nucleic acid molecule.

9. The method of claim 8, wherein the promoter is a polII or polIII RNA promoter.

10. The method of claim 8, wherein the expression cassette is present in an expression vector.

11. The method of claim 1, wherein the mutant CAG expanded gene allele is an allele of a gene that causes Huntington disease or spinocerebellar ataxia type 3.

12. The method of claim 11, wherein the cell is cultured in vitro.

13. The method of claim 12, wherein the nucleic acid molecule is introduced into the cell in vivo.

14. A method of treating a neurological disease chosen from Huntington disease and spinocerebellar ataxia type 3 in a subject in need thereof, comprising inhibiting expression of a mutant CAG expanded gene allele in a cell of the subject by the method of claim 1.

* * * * *

UNITED STATES PATENT AND TRADEMARK OFFICE
CERTIFICATE OF CORRECTION

PATENT NO.      : 9,970,004 B2
APPLICATION NO. : 14/916039
DATED           : May 15, 2018
INVENTOR(S)     : Wlodzimierz Krzyzosiak et al.

Page 1 of 1

It is certified that error appears in the above-identified patent and that said Letters Patent is hereby corrected as shown below:

On the Title Page

Item [54], delete "INTERFERENCDE" and insert --INTERFERENCE--

Signed and Sealed this
Twenty-eighth Day of January, 2020

Andrei Iancu
*Director of the United States Patent and Trademark Office*